United States Patent [19]

Sullivan et al.

[11] 4,158,440
[45] Jun. 19, 1979

[54] DEVICE FOR RELEASING A VOLATILE SUBSTANCE IN A CONTROLLED MANNER

[75] Inventors: William E. Sullivan; Murray O. Meetze, Jr., both of Columbia, S.C.

[73] Assignee: The Ridson Manufacturing Company, Naugatuck, Conn.

[21] Appl. No.: 731,300

[22] Filed: Oct. 12, 1976

[51] Int. Cl.² .............................................. A61L 9/04
[52] U.S. Cl. ........................................ 239/1; 239/56
[58] Field of Search .............. 239/34, 44, 51.5, 53–57, 239/1, 60; 260/13, 17 A

[56] References Cited

U.S. PATENT DOCUMENTS

| | | | |
|---|---|---|---|
| 2,988,284 | 6/1961 | Smith | 239/54 |
| 3,770,199 | 11/1973 | Hoek et al. | 239/54 |
| 3,846,404 | 11/1974 | Nichols | 260/17 A |
| 3,858,807 | 1/1975 | Rabussier et al. | 239/56 |
| 3,940,062 | 2/1976 | Rainey | 239/56 |

FOREIGN PATENT DOCUMENTS 1436075  5/1976  United Kingdom ...................... 239/54

Primary Examiner—Robert B. Reeves
Assistant Examiner—Andres Kashnikow
Attorney, Agent, or Firm—St. Onge, Steward, Johnston, Reens & Nöe

[57] ABSTRACT

A device for releasing a volatile substance into the environment in a controlled manner comprises a reservoir of substance-absorbent material, for storing the substance, that is encapsulated in an envelope, at least a portion of which comprises a permeable material having porosity at least equal to ultramicroporosity. The permeable envelope portion has a greater affinity for the substance than does the reservoir material. The remainder of the envelope comprises a material impermeable to the substance. Accordingly, the substance permeates through the permeable envelope portion to be released therefrom in vapor form into the environment.

2 Claims, 4 Drawing Figures

DEVICE FOR RELEASING A VOLATILE SUBSTANCE IN A CONTROLLED MANNER

BACKGROUND OF THE INVENTION

1. Field of the Invention

The present invention relates to a device for releasing a volatile substance into the environment in a controlled manner. In particular, this invention contains the volatile substance to prevent its spilling or oozing and provides a way of releasing multicomponent substances in a uniform, continuous manner.

Many consumer products such as room deodorizers, insecticides, germicides, fragrances and the like are volatile and may be released and dispersed in an area to be treated merely by being exposed therein. Devices for dispensing these products are available in many forms such as liquid and wick systems, blotter systems and gel systems. However, the volatile substance may be subject to spillage, oozing or waste in each of these systems.

2. Description of the Prior Art

Various devices and methods for containing a volatile substance and for controlling the release of vapor from the substance are presently known. For example, U.S. Pat. No. 3,770,199 (Hoek et al.) discloses a device for the controlled emission of vapors which has an inner tubular or box-shaped member telescopically arranged in a second tubular box-shaped outer member so that the inner member may be entirely or partially sealed by the outer member. A porous container, preferably made of polyethylene, is mounted within the inner member and may be filled with an active substance. The inner member may be either apertured or also made of a porous material such as polyethylene. When the inner member is open outwardly of the outer member, the liquid active substance is vaporized inside the container and permeates through both the container and the inner member. This device operates in a fashion similar to wick devices in that the rate of volatilization of the substance may be controlled by the amount of inner member, or wick, exposed from the outer member.

U.S. Pat. No. 2,988,284 (Smith) discloses a device which includes a block made from a substance such as wood, cellulose, fiber, pulp, filament, silicate, gum, plastic or the like, which is impregnated with a fragrance and is hermetically sealed in an air-tight vapor impermeable coating. A hole or holes are drilled into the block through the coating and fragrance is emitted therefrom. Vaporization of the fragrance is controlled by the relatively small exposed surface area of the hole compared to the volume of the entire block.

U.S. Pat. No. 3,685,734 (Paciorek et al.) discloses a controlled fragrance release device which includes a substrate layer on which a layer of vinyl plastisol resin containing an essential oil or other volatile substance is coated. A cover ply is placed over the resin layer to contain the volatile substance until removed.

Another approach to controlling release of volatile substances is disclosed in U.S. Pat. No. 3,216,882 (Feldt et al.) and in U.S. Pat. No. 4,035,451 (Tringali), assigned to the assignee of the present invention. The Feldt patent discloses a porous plastic film which may be impregnated with a volatile substance to be slowly released therefrom. The Tringali patent application discloses a cartridge having a support of strip material and a battery. The cartridge is adapted for use with an apparatus for inducing air flow past the support of strip material which is impregnated with a volatile substance. This support may be a gelled cellulose triacetate product made in accordance with U.S. Pat. No. 3,846,404 (Nichols).

These latter approaches to containing and controlling release of volatile substances have certain disadvantages. In particular, porous, microporous and ultramicroporous film strips are relatively expensive. Therefore, though effective to contain and release volatile substances, they are uneconomical for use in applications where large amounts of such substances are to be initially held for later volatization into an environment.

Another significant problem with each of these devices arises when a substance having several chemical components, each having a different rate of vaporization, is dispensed. Especially in the case of multicomponent fragrances when the various components volatilize at different rates, the intensity of the fragrance as well as the fragrance itself may change with time. Therefore, an initially pleasant fragrance may lose its desirable attributes.

SUMMARY OF THE INVENTION

In a preferred embodiment, to be described below in detail, the device of the present invention contains a volatile substance for release into the environment in a controlled manner. Specifically, this device prevents spillage and oozing of a volatile liquid substance so that it can be released into the environment as desired. Moreover, the device takes advantage of the beneficial characteristics of microporous and ultramicroporous materials such as gelled cellulose triacetate disclosed in U.S. Pat. No. 3,846,404 (Nichols), yet, only small amounts of the ultramicroporous and microporous materials need be used to dispense relatively large amounts of volatile substances into an environment. Accordingly, the device of the present invention may be put into widespread use at substantially lower cost then devices in which fragrances are directly impregnated in continuous masses of such materials.

In one preferred embodiment, the device of the present invention comprises a reservoir of volatile substance-absorbent material, for storing the substance, that is encapsulated in an envelope. At least a portion of the envelope comprises a permeable material which has porosity at least equal to ultramicroporosity and further has a greater affinity for the non-vapor phase of the substance than does the reservoir material. The remainder of the envelope comprises a material impermeable to the substance. Accordingly, the non-vapor phase of the substance preferentially migrates through the permeable envelope portion and is volatilized from the exterior surface of that portion to be released into the environment.

Alternatively, a microporous or ultramicroporous envelope portion may be employed which acts as a liquid barrier permitting only the vapor from the substance to escape therethrough.

In both cases, it has been found that substantially all of the volatile substance originally stored in the reservoir is diffused into the environment by the interaction of the reservoir material and the material of which the permeable envelope portion is made. Accordingly, little waste of the volatile substance occurs. Furthermore, since the reservoir serves the major substance-storing function and relatively small amounts of ultramicroporous or porous material are used in the device, it may be constructed at far less cost than devices which are composed in their entireties of such materials.

When substances having several chemical components with different rates of vaporization are to be released into the environment, the device may be made with several compartments, each for containing and releasing one of the components. The surface area of microporous or ultramicroporous material exposed in each compartment is adjusted relative to other compartments so that all components are released at the same rate. In this way the substance, as a whole, can be released uniformly over an extended period of time.

Accordingly, it is an object of the present invention to provide a device for releasing a volatile substance into the environment in a controlled manner which utilizes substantially all of the substance that it originally contains. It is a further object of the present invention to provide an economically constructed device which uses a minimum of relatively expensive microporous or ultramicroporous material. Another object of the invention is to release even multicomponent volatile substances uniformly.

Other objects, aspects, and advantages of the present invention will be pointed out in or will be understood from the following detailed description provided below in conjunction with the accompanying drawings.

DETAILED DESCRIPTION OF THE PREFERRED EMBODIMENTS

Figure 1:
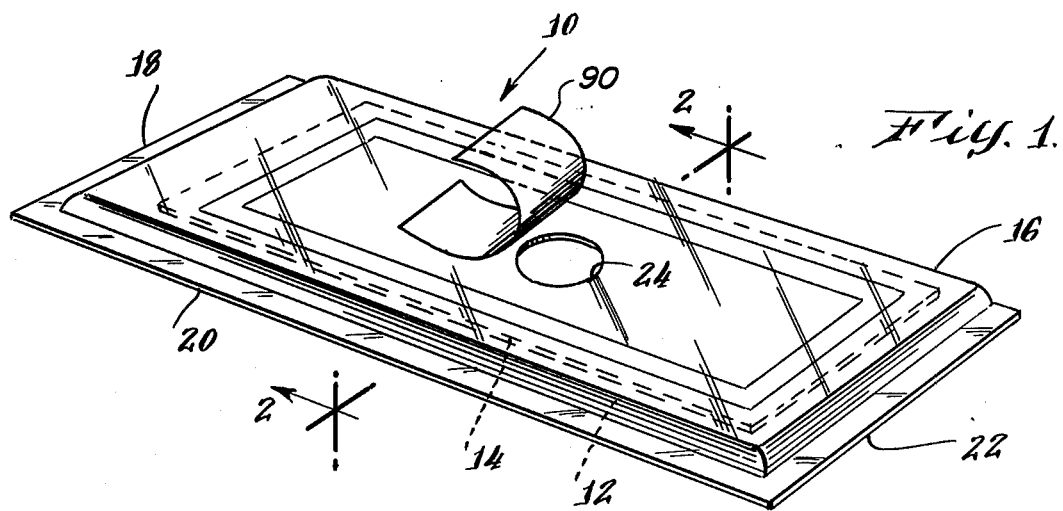
FIG. 1 is a perspective view of one embodiment of the device for releasing a volatile product into the environment in a controlled manner in accordance with the present invention.
Figure 2:
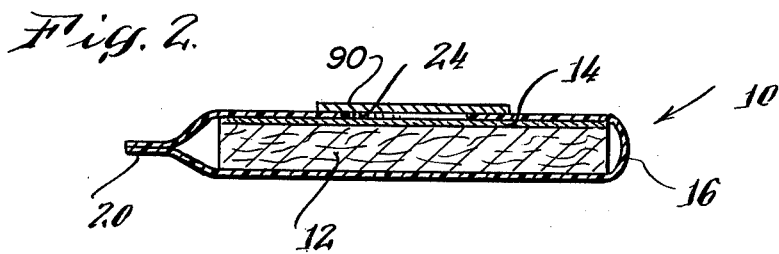
FIG. 2 is a vertical cross-sectional view of this embodiment of the device taken through plane 2—2 in FIG. 1.

As can be seen in FIGS. 1 and 2, the device, generally indicated at 10, for releasing a volatile substance into the environment in a controlled manner, comprises a reservoir 12 which may be in the form of a relatively thick pad of felt material. Alternatively, the reservoir may be an open cell natural or cellulose sponge or any other suitable material which is absorbent of the volatile substance that may be, for example, a fragrance, an insecticide, a germicide, or the like.

A sheet of ultramicroporous material 14 and, in particular, gelled cellulose triacetate available from Moleculon Research Corporation, Cambridge, Mass. and constructed in accordance with U.S. Pat. No. 3,846,404 (Nichols), is placed in contact with the top of the reservoir 12 and functions in a manner to be described below to exhaust the volatile substance from the reservoir.

After the reservoir 12 has been filled with the volatile substance to be dispensed, it and the ultramicroporous sheet 14 are encapsulated in an envelope 16 which is impermeable to the volatile substance. In the preferred embodiment this envelope is a non-porous polypropylene film which is folded over both top and bottom of the ultramicroporous sheet and reservoir assembly and is heat sealed along the three edges 18, 20 and 22 to completely contain the assembly.

When the envelope 16 is sealed about the reservoir-ultramicroporous sheet assembly, the periphery of the sheet is heat sealed to the polypropylene film in contact therewith. A hole 24 is then cut through the film within the heat sealed periphery to expose at least a portion of the ultramicroporous sheet to the environment.

It can be readily appreciated from the drawings that the volume of the reservoir is substantially greater than the volume of the ultramicroporous sheet 14. Accordingly, the reservoir is capable of storing an amount of volatile substance much greater than that which might be impregnated in the strip.

Further, it has been found that when a device is constructed in the fashion described above, with the materials specified, a preferential migration of the volatile substance takes place through the ultramicroporous material 14 from the reservoir 12. Moreover, this migration is of the substance in its non-vapor, that is, usually liquid form. Vaporization of the liquid then takes place on the exterior surface of the material 14 for subsequent diffusion into the area to be treated.

It is believed that the ultramicroporous material has a greater affinity for the volatile substance than the larger porous reservoir. Moreover, it has been found that the preferential migration described above essentially exhausts all of the substance originally stored in the reservoir so that little or none is wasted when the device is discarded.

The device of the present invention provides more uniform, continuous release of the volatile substance than a device composed of ultramicroporous material alone. For example, pores in gelled cellulose triacetate tend to collapse as a volatile substance is exhausted from it. Therefore, the release rate slows as more of the substance is used up. However, in the device of the invention, the substance tends to migrate through the ultramicroporous sheet at a uniform rate. That is, the amount of substance in the sheet at any one time is substantially constant until the reservoir is nearly exhausted. Thus, a continuous uniform substance release rate is maintained for an extended period of time while the relatively large amount of substance initially present in the reservoir is volatilized.

It has also been found that a microporous polypropylene film material sold under the name "Celgard" by the Celanese Corporation is also suitable for use in place of the film material available from Moleculon Research Corporation. However, the Celgard film material acts as a liquid barrier, being permeable only to vapor which volatilizes from the substance. Accordingly, vaporization takes place within the reservoir and the vapor is ultimately permeated through the microporous sheet.

In addition, ultramicroporous or microporous polyethylene film may be used as the sheet through which the volatile substance passes. Polyethylene is particularly well suited for dispensing highly volatile substances since it permits volatilization only at a very slow rate.

The reservoir of the device described above may be filled at any time prior to final sealing of the envelope. Thus devices may be fully assembled and charged with a volatile substance in one manufacturing operation. However, the device may be made in uncharged form to be filled with a volatile substance at a later time. In order to do so, the permeable sheet is first impregnated with an expendable substantially non-volatile substitute substance to prevent collapse of its pores. This is particularly important when gelled cellulose triacetate is used as the microporous sheet material since once a volatile substance has been exhausted therefrom, its pores collapse and cannot be reexpanded. The non-volatile substitute substance should be soluble in or a solute for the volatile substance which will later be added to the reservoir. In this fashion, the device may be made and the ultramicroporous film preserved until such later time as the device is to be charged with the volatile substance. The volatile substance may then dissolve the substitute substance to be released in the manner described above.

As noted above, problems have arisen in the past in controlling release of volatile substances which have several chemical constituents which exhibit different rates of vaporization. The device of the present invention may be adapted to release such substances in a uniform manner so that the characteristics of their vapor remain substantially constant over extended periods of time. Such an adaptation forms a second embodiment of the present invention and is illustrated in FIGS. 3 and 4.

The device of this second embodiment is adapted to dispense a substance having three volatile chemical constituents which may be separated by, for example, distillation or may be purchased separately. The device, generally indicated at 50, therefore, has three compartments 52, 54 and 56, one for each of the constituents. In general, each compartment of the device is made in the same way as that described with reference to the first embodiment and includes a non-porous polypropylene envelope 57 which is folded about three separate volatile subtance constituent-absorbent felt reservoirs 58, 60 and 62. Further, separate microporous or ultramicroporous sheets 64, 66 and 68 are laid over each of the reservoirs. The envelope 57 is folded over the respective reservoir-ultramicroporous sheet assemblies and is heat sealed at three edges 70, 72 and 74 and along two separating barriers 76 and 78 so that each of the assemblies is independent of the others. Again, the periphery of each ultramicroporous sheet is heat sealed to the envelope at the point of mutual contact therebetween. Holes 80, 82 and 84 are cut through the envelope within each of the respective heat sealed peripheries to expose the associated ultramicroporous sheet to the environment.

Figure 3:
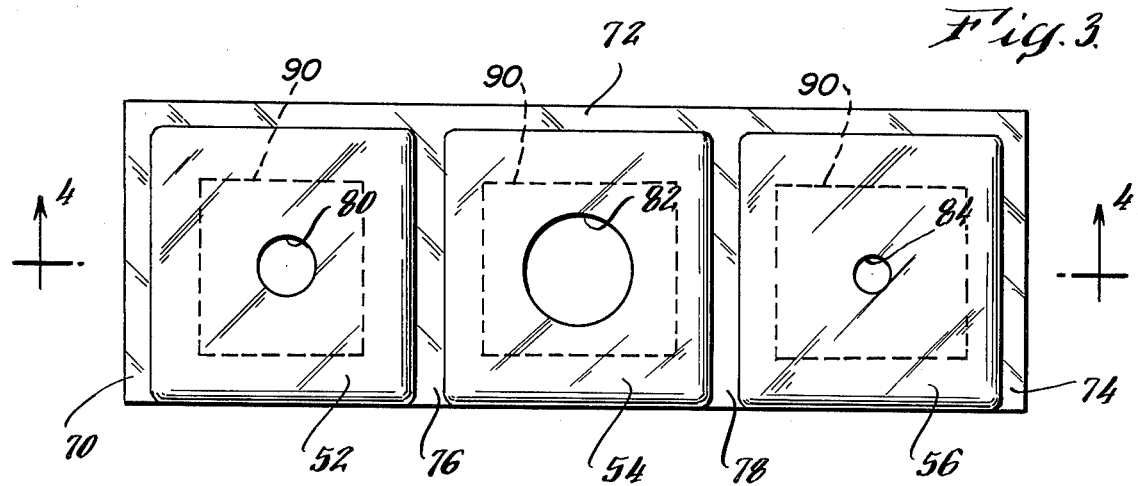
FIG. 3 is a top plan view of a second embodiment which is a multicompartment device constructed in accordance with the invention for uniformly releasing a multicomponent substance.
Figure 4:
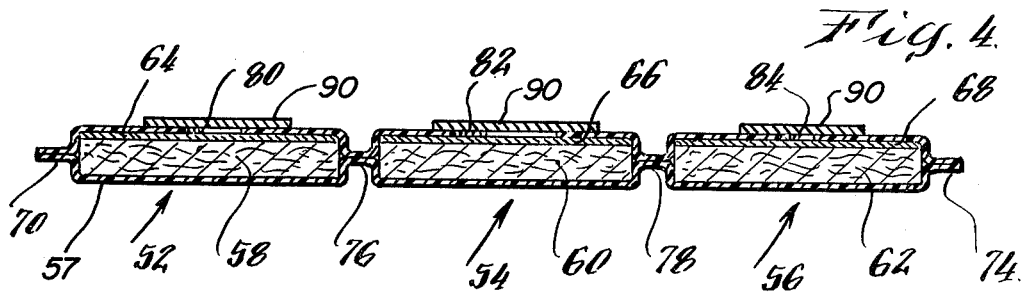
FIG. 4 is a vertical cross-sectional view taken through plane 4—4 in FIG. 3.

As can be seen in FIGS. 3 and 4, the respective holes are of different sizes, the size of each being inversely proportional to the rate of vaporization of the constituent of the substance to be filled in each respective reservoir. Thus, for example the compartment in the center has an extremely large hole 82 to enhance volatilization of a substance constituent which ordinarily has a slow rate of vaporization. Conversely, the right compartment 56 has a small hole 84 to slow release of a constituent having a normally rapid rate of vaporization. The left component has an intermediate size hole for a constituent having an intermediate right of vaporization. By calculating the respective rates of vaporization of the respective components, and adapting the hole size in the compartment for housing that constituent, each constituent and hence the entire substance may be volatilized at a substantially uniform rate to maintain a substantially uniform fragrance, germicidal effect, insecticidal effect or the like depending on the substance filling the device. Accordingly, the second embodiment represents a substantial improvement over prior art devices for controlling release of a volatile substance.

Of course, the second embodiment may be made in a manner described with reference to the first embodiment so that it may be charged at a later time with various different volatile substances. Moreover, both the first and second embodiment, once charged or filled should be maintained in an air-tight environment until ready for use. Thus, the device may be sealed in an air-tight container or may be provided with a self-adhering, removable covering 90 (FIG. 1) for the respective holes which expose the ultramicroporous or microporous sheets to the environment.

Accordingly, although specific embodiments of the present invention have been described above in detail, it is to be understood that this is for purposes of illustration. Modifications may be made to the described structures by those skilled in the art in order to adapt the devices for releasing volatile substances into the environment in a controlled manner to particular applications.

What is claimed is:

1. A method for filling a device for releasing a volatile substance into the environment in a controlled manner, the device comprising a reservoir of substance-absorbent material and an envelope encapsulating the reservoir, at least a portion of which has porosity at least equal to ultramicroporosity and a greater affinity for the volatile substance than does the reservoir, said method comprising the steps of:
   A. impregnating a substantially non-volatile substitute substance in the permeable envelope portion, one of the substitute substance and volatile substances being soluble in the other of said substances, and
   B. introducing, at a later time, the volatile substance into the reservoir, whereby the device may be assembled a substantial time prior to introduction of said volatile substance into the reservoir without damage to said permeable envelope portion.

2. A device for releasing a volatile substance into the environment in a controlled manner, said device comprising:
   A. a reservoir of substance-absorbent material;
   B. an envelope encapsulating said reservoir,
      1. at least a portion of said envelope comprising a permeable material which has porosity at least equal to ultramicroporosity and a greater affinity for the substance than does said reservoir material,
      2. The remainder of said envelope comprising a material impermeable to the substance, and
   C. a substantially non-volatile substitute substance impregnated in said permeable envelope portion, one of said substitute substance and volatile substance being soluble in the other of said substances, whereby said reservoir may be filled with volatile substance after assembly of said device and whereby when the device is filled, the volatile substance permeates through said permeable envelope portion to dissolve said substitute substance and be released in vapor form into the environment.

* * * * *